US012269484B2

(12) United States Patent
Butters et al.

(10) Patent No.: US 12,269,484 B2
(45) Date of Patent: Apr. 8, 2025

(54) SYSTEMS AND METHODS TO KEEP DRIVERS, PILOTS, OR OTHERS ALERT OR FOCUSED BY ELECTROMAGNETIC DELIVERY OF SIGNALS

(71) Applicant: NearField Atomics Inc., Seattle, WA (US)

(72) Inventors: John T. Butters, Seattle, WA (US); Lisa C. Butters, Seattle, WA (US)

(73) Assignee: NearField Atomics Inc., Seattle, WA (US)

( * ) Notice: Subject to any disclaimer, the term of this patent is extended or adjusted under 35 U.S.C. 154(b) by 251 days.

(21) Appl. No.: 17/677,269

(22) Filed: Feb. 22, 2022

(65) Prior Publication Data

US 2022/0274604 A1    Sep. 1, 2022

Related U.S. Application Data

(60) Provisional application No. 63/252,986, filed on Oct. 6, 2021, provisional application No. 63/164,022, filed (Continued)

(51) Int. Cl.
*B60W 40/09*    (2012.01)
*B60N 2/00*    (2006.01)

(52) U.S. Cl.
CPC .......... *B60W 40/09* (2013.01); *B60N 2/0022* (2023.08); *B60N 2230/20* (2023.08); *B60W 2540/22* (2013.01); *B60W 2540/229* (2020.02)

(58) Field of Classification Search
CPC ............. B60W 40/09; B60W 2540/22; B60W 2540/229; B60W 2510/20;

(Continued)

(56) References Cited

U.S. PATENT DOCUMENTS 6,541,978 B1    4/2003    Benveniste et al.
6,724,188 B2    4/2004    Butters et al.
(Continued)

FOREIGN PATENT DOCUMENTS

DE    102014218744    3/2016
EP    2109771 B1    6/2010
(Continued)

OTHER PUBLICATIONS

"Theobromine," Wikipedia, The Free Encyclopedia, https://en.wikipedia.org/wiki/theobromine (accessed Feb. 23, 2024) (Year: 2024).*

(Continued)

*Primary Examiner* — Ashley L Redhead, Jr.
(74) *Attorney, Agent, or Firm* — Branch Partners PLLC; Bruce E. Black

(57) ABSTRACT

A system for delivery of ultra-low radio frequency energy to an individual to assist the individual to remain, or become, alert, awake, or focused includes at least one delivery coil and a delivery device that includes at least one memory; at least one data file configured for producing signals derived from measurements of at least one molecule; and at least one processor coupled to the at least one memory and the at least one delivery coil. The at least one processor is configured to perform actions that include directing generation of the signals using the at least one data file and directing delivery of the signals to the at least one delivery coil to produce the ultra-low radio frequency energy.

20 Claims, 9 Drawing Sheets

Related U.S. Application Data on Mar. 22, 2021, provisional application No. 63/154,532, filed on Feb. 26, 2021.

(58) Field of Classification Search
CPC ....... B60W 2540/215; B60W 2520/10; B60W 2040/0818; B60W 2540/221; B60W 2540/223; B60W 2540/225; G01N 37/005; G08B 21/06; A61B 5/021; A61B 5/024; A61B 5/11; A61B 5/14542; A61B 5/162; A61B 5/163; A61B 5/168; A61B 5/346; A61B 5/369; A61B 5/7267; A61B 2503/22; A61B 5/165; A61B 5/18; A61B 5/6893; B60N 2002/981; B60N 2/002; B60N 2/976; A61N 1/40; A61N 2/02; A61N 2/004; B60K 28/066
See application file for complete search history.

(56) References Cited

U.S. PATENT DOCUMENTS

| | | | |
|---|---|---|---|
| 6,952,652 B2 | 10/2005 | Butters | |
| 6,995,558 B2 | 2/2006 | Butters et al. | |
| 7,048,890 B2 | 5/2006 | Coehoorn et al. | |
| 7,081,747 B2 | 7/2006 | Butters et al. | |
| 7,412,340 B2 | 8/2008 | Butters | |
| 8,456,157 B2 | 6/2013 | Litvinov et al. | |
| 8,494,198 B2 | 7/2013 | Aldaz et al. | |
| 8,838,022 B2 | 9/2014 | Dobyns | |
| 8,929,809 B2 | 1/2015 | Dobyns | |
| 9,300,367 B2 | 3/2016 | Christensen et al. | |
| 9,417,257 B2 | 8/2016 | Butters et al. | |
| 9,455,771 B2 | 9/2016 | Dobyns | |
| 9,742,471 B1 | 8/2017 | Thoen | |
| 10,012,706 B2 | 7/2018 | Bates et al. | |
| 10,015,623 B2 | 7/2018 | Thoen | |
| 10,046,172 B2 | 8/2018 | Butters et al. | |
| 10,210,409 B1 | 2/2019 | Migneco et al. | |
| 10,715,937 B2 | 7/2020 | Haubrich et al. | |
| 10,939,488 B2 | 3/2021 | Ng et al. | |
| 11,103,721 B2 | 8/2021 | Butters et al. | |
| 2002/0077537 A1 | 6/2002 | Arvin et al. | |
| 2004/0233060 A1* | 11/2004 | Mohri | A61B 5/1103 340/575 |
| 2005/0087000 A1 | 4/2005 | Coehoorn et al. | |
| 2007/0148670 A1* | 6/2007 | O'Malley | C12Q 1/6825 435/7.1 |
| 2008/0097142 A1 | 4/2008 | Savage | |
| 2010/0097186 A1 | 4/2010 | Wielebski et al. | |
| 2010/0264917 A1 | 10/2010 | Budker et al. | |
| 2010/0298624 A1 | 11/2010 | Becker | |
| 2011/0148640 A1* | 6/2011 | Kang | H04B 13/005 340/573.1 |
| 2011/0244599 A1 | 10/2011 | Whig et al. | |
| 2012/0136585 A1* | 5/2012 | Apostolos | G01V 3/14 702/23 |
| 2012/0310550 A1 | 12/2012 | Bates et al. | |
| 2013/0261374 A1 | 10/2013 | Elder | |
| 2013/0324786 A1 | 12/2013 | Rogachefsky | |
| 2014/0029777 A1 | 1/2014 | Jang | |
| 2014/0292318 A1 | 10/2014 | Wang et al. | |
| 2015/0335288 A1* | 11/2015 | Toth | A61B 5/6833 600/391 |
| 2016/0008632 A1 | 1/2016 | Wetmore et al. | |
| 2016/0011183 A1 | 1/2016 | Egan et al. | |
| 2016/0028493 A1* | 1/2016 | Ohishi | H04B 13/005 455/41.2 |
| 2016/0030761 A1 | 2/2016 | Butters et al. | |
| 2017/0067969 A1 | 3/2017 | Butters et al. | |
| 2017/0097337 A1 | 4/2017 | Schultz et al. | |
| 2017/0117972 A1* | 4/2017 | Ishibashi | H04B 13/005 |
| 2017/0164834 A1* | 6/2017 | Park | A61B 5/4839 |
| 2017/0207860 A1* | 7/2017 | Zhang | H04B 13/005 |
| 2017/0244496 A1* | 8/2017 | Geurts | H04L 63/10 |
| 2017/0266443 A1 | 9/2017 | Rajguru et al. | |
| 2017/0343695 A1 | 11/2017 | Stetson et al. | |
| 2018/0237850 A1 | 8/2018 | Mandell et al. | |
| 2018/0353095 A1 | 12/2018 | Boesen | |
| 2019/0015048 A1 | 1/2019 | Baker et al. | |
| 2019/0143135 A1 | 5/2019 | Butters | |
| 2019/0184188 A1 | 6/2019 | Butters et al. | |
| 2019/0317167 A1 | 10/2019 | Laborde et al. | |
| 2020/0086078 A1* | 3/2020 | Poltorak | A61N 1/36025 |
| 2020/0295848 A1* | 9/2020 | Kang | H04B 13/005 |
| 2020/0326309 A1 | 10/2020 | Braganca et al. | |
| 2021/0204867 A1* | 7/2021 | Toth | A61B 5/0002 |
| 2022/0226663 A1 | 7/2022 | Butters et al. | |
| 2022/0257962 A1 | 8/2022 | Mogen et al. | |
| 2022/0274604 A1* | 9/2022 | Butters | A61N 2/004 |
| 2023/0201615 A1 | 6/2023 | Figueroa et al. | |
| 2023/0240529 A1* | 8/2023 | Toth | G06F 11/3093 600/301 |
| 2024/0189612 A1 | 6/2024 | Butters | |

FOREIGN PATENT DOCUMENTS

| | | |
|---|---|---|
| EP | 2115468 B1 | 6/2010 |
| EP | 1566651 B1 | 6/2013 |
| EP | 2614770 | 7/2013 |
| EP | 2800970 B1 | 9/2016 |
| EP | 3695878 | 8/2020 |
| WO | 2014/184395 A9 | 11/2014 |
| WO | 2019/070911 | 4/2019 |
| WO | 2019/140404 | 7/2019 |
| WO | 2019/142196 | 7/2019 |

OTHER PUBLICATIONS

"Stimulant," Wikipedia, The Free Encyclopedia, https://en.wikipedia.org/wiki/stimulant (accessed Feb. 23, 2024) (Year: 2024).*

International Search Report and Written Opinion for PCT/US2022/017246 mailed May 19, 2022.

International Search Report and Written Opinion for PCT Application No. PCT/US2022/020384 mailed Jun. 29, 2022.

Issadore D, Park Yi, Shao H, Min C, Lee K, Liong M, Weissleder R, Lee H. Magnetic sensing technology for molecular analyses. Lab Chip. Jul. 21, 2014;14(14):2385-97. doi: 10.1039/c4lc00314d.

Oogane, M., Fujiwara, K., Kanno, A., Nakano, T., Wagatsuma, H., Arimoto, T., Mizukami, S., Kumagai, S., Matsuzaki, H., Nakasato, N., & Ando, Y. (2021). Sub-pT magnetic field detection by tunnel magneto-resistive sensors. Applied Physics Express, 14(12), [123002]. https://doi.org/10.35848/1882-0786/ac3809.

Richard S. Gaster; Giant Magnetoresistive Nanosensors for Ultrasensitive In Vitro Diagnostics and Biomolecular Kinetics. Dissertation submitted to Stanford University, Nov. 2011; 163 pages. Available on-line at https://purl.stanford.edu/jt093nq0893.

Adem S, Jain S, Sveiven M, Zhou X, O'Donoghue AJ, Hall DA. Giant magnetoresistive biosensors for real-time quantitative detection of protease activity. Sci Rep. May 14, 2020;10(1):7941. doi: 10.1038/s41598-020-62910-2. PMID: 32409675; PMCID: PMC7224196.

Wang, W., Wang, Y., Tu, L. et al. Magnetoresistive performance and comparison of supermagnetic nanoparticles on giant magnetoresistive sensor-based detection system. Sci Rep 4, 5716 (2014). https://doi.org/10.1038/srep05716.

Rizzi, G., Dufva, M. & Hansen, M. Magnetoresistive sensors for measurements of DNA hybridization kinetics—effect of TINA modifications. Sci Rep 7, 41940 (2017). https://doi.org/10.1038/srep41940.

Trisnanto, Suko & Kasajima, Tamon & Akushichi, Taiju & Takemura, Yasushi. (2021). Magnetic particle imaging using linear magnetization response-driven harmonic signal of magnetoresistive sensor. Applied Physics Express. 14. 10.35848/1882-0786/ac1d63.

Ioanna Giouroudi and Evangelos Hristoforou , "Perspective: Magnetoresistive sensors for biomedicine", Journal of Applied Physics 124, 030902 (2018) https://doi.org/10.1063/1.5027035.

Baselt DR, Lee GU, Natesan M, Metzger SW, Sheehan PE, Colton RJ. A biosensor based on magnetoresistance technology. Biosens

(56) References Cited

OTHER PUBLICATIONS

Bioelectron. Oct. 1, 1998;13(7-8):731-9. doi: 10.1016/s0956-5663(98)00037-2. PMID: 9828367.

Yao, Li & Xu, Shoujun. (2014). Detection of magnetic nanomaterials in molecular imaging and diagnosis applications. Nanotechnology Reviews. 3. 247-268. 10.1515/ntrev-2013-0044.

Yin, T.-I & Paul, J. & Lehndorff, Ronald. (2016). 3.3.1—Magnetoresistive Sensors for the Application in Biotechnology. 190-194. 10.5162/sensoren2016/3.3.1.

Shirai Y, Hirao K, Shibuya T, Okawa S, Hasegawa Y, Adachi Y, Sekihara K, Kawabata S. Magnetocardiography Using a Magnetoresistive Sensor Array. Int Heart J. Jan. 25, 2019;60(1):50-54. doi: 10.1536/ihj. 18-002. Epub Nov. 20, 2018. PMID: 30464123.

Smith, C.H., & Schneider, R.W. (2000). GMR and SDT Sensors and Arrays for LowField Magnetic Applications. Nonvolatile Electronics, Inc. 12 pages.

Bae, Seongtae. (2010). In-Vitro Magnetoresistive Biosensors for Single Molecular Based Disease Diagnostics: Optimization of Sensor Geometry and Structure. 10.5772/6870.

Henriksen, Anders & Ley, Mikkel & Flyvbjerg, Henrik & Hansen, Mikkel. (2015). Configurational Statistics of Magnetic Bead Detection with Magnetoresistive Sensors. PloS one. 10. e0141115. 10.1371/journal.pone.0141115.

Reiss, Guenter & Brückl, Hubert & Hutten, Andreas & Schotter, Joerg & Brzeska, Monika & Panhorst, Michael & Sudfeld, Daniela & Becker, Anke & Kamp, Paul-Bertram & Puehler, Alfred & Wojczykowski, Klaus & Jutzi, Peter. (2004). Magnetoresistive Sensors and Magnetic Nanoparticles for Biotechnology. Journal of Materials Research. 20. 3294-3302. 10.1557/PROC-853-I9.1.

Su D, Wu K, Saha R, Peng C, Wang JP. Advances in Magnetoresistive Biosensors. Micromachines (Basel). Dec. 26, 2019;11(1):34. doi: 10.3390/mi11010034. PMID: 31888076; PMCID: PMC7019276.

Ulasov IV, Foster H, Butters M, Yoon JG, Ozawa T, Nicolaides T, Figueroa X, Hothi P, Prados M, Butters J, Cobbs C. Precision knockdown of EGFR gene expression using radio frequency electromagnetic energy. J Neurooncol. Jun. 2017;133(2):257-264. doi: 10.1007/s11060-017-2440-x. Epub Apr. 22, 2017. PMID: 28434113.

Butters, John & Figueroa, Xavier & Butters, Bennett. (2014). Non-Thermal Radio Frequency Stimulation of Tubulin Polymerization in Vitro: A Potential Therapy for Cancer Treatment. Open Journal of Biophysics. 04. 147. 10.4236/ojbiphy.2014.44015.

Mukthavaram R, Jiang P, Nomura N, et al. ATPS-64: Preclinical Studies Using Nativis Voyager RFE System, a Novel Non-Invasive, Low Energy, Non-Thermal, Non-Ionizing Radiofrequency Energy (RFE) Device in Glioblastoma Mouse Models. Neuro Oncol. 2015;17(Suppl 5):v32. doi:10.1093/neuonc/nov204.64.

Cobbs C, McClay E, Duic JP, Nabors LB, Morgan Murray D, Kesari S. An early feasibility study of the Nativis Voyager® device in patients with recurrent glioblastoma: first cohort in US. CNS Oncol. Mar. 2019;8(1):CNS30. doi: 10.2217/cns-2018-0013. Epub Dec. 14, 2018. PMID: 30547676; PMCID: PMC6499016.

Murphy M, Dowling A, Thien C, Priest E, Morgan Murray D, Kesari S. A feasibility study of the Nativis Voyager® device in patients with recurrent glioblastoma in Australia. CNS Oncol. Mar. 2019;8(1):CNS31. doi: 10.2217/cns-2018-0017. Epub Feb. 7, 2019. PMID: 30727742; PMCID: PMC6499017.

Ulasov, Ilya & Ghosh, Dhimankrishna & Butters, Mike & Butters, John & Cobbs, Charles. (2016). EXTH-50. Specific Knockdown of EGFR and PLK1 Gene Expression in U87 GBM Cells With Radiofrequency Energy (RFE) Device. Japan Society for Neuro-Oncology. 18. vi70-vi70. 10.1093/neuonc/now212.292.

Butters, Bennett & Vogeli, Gabriel & Figueroa, Xavier. (2017). Non-Thermal Radio Frequency Stimulation Inhibits the Tryptophan Synthase Beta Subunit in the Algae Chlamydomonas reinhardtii. Open Journal of Biophysics. 07. 82-93. 10.4236/ojbiphy.2017.73007.

Figueroa, Xavier; Green, Yesenia; Murray, Donna Morgan; and Butters, Mike. Effects of Magnetic Fields on Biological Systems, An Overview. EMulate Therapeutics, Mar. 6, 2020. 8 pages.

Figueroa, Xavier & Butters, Mike & Donnell, Scott. (2019). SCIDOT-47. Effect of uIRFE Cognates Emulating Bioactive Substances on Animal Behavior. Neuro-Oncology. 21. vi281-vi282. 10.1093/neuonc/noz175.1183.

Specification of U.S. Appl. No. 17/695,482, filed Mar. 15, 2022.

Press Release for "Hapbee Announces Filing of Provisional Patent Application for Bed-Related Form Factor," Feb. 19, 2021, found at https://hapbee.com/blogs/hapbee/hapbee-announces-filing-of-provisional-patent-application-for-bed-related-form-factor.

Andrew Kelly, "Integrated Circuit Design for Miniature Implantable Medical Devices," Presented at the Embedded Systems Conference at Design East in Boston, MA. Sep. 18, 2012. 14 pages.

Kim, Han-Joon, et al. "Review of near-field wireless power and communication for biomedical applications." IEEE Access, vol. 5, 2017, pp. 21264-21285, https://doi.org/10.1109/access.2017.2757267. (Year: 2017).

* cited by examiner

SYSTEMS AND METHODS TO KEEP DRIVERS, PILOTS, OR OTHERS ALERT OR FOCUSED BY ELECTROMAGNETIC DELIVERY OF SIGNALS

CROSS-REFERENCE TO RELATED APPLICATIONS

This patent application claims priority to U.S. Provisional Patent Application Ser. No. 63/154,532, filed Feb. 26, 2021; 63/164,022, filed Mar. 22, 2021; and 63/252,986, filed Oct. 6, 2021, all of which are incorporated herein by reference in their entireties.

FIELD

The present invention is directed to the area of systems and methods for assisting individuals in remaining alert, awake, focused, or otherwise stimulated by electromagnetic delivery of signals from a data file. The present invention is also directed to systems and methods for delivery of electromagnetic signals arising from measurements using a stimulant to facilitate assisting individuals in remaining alert, awake, focused, or otherwise stimulated.

BACKGROUND

Drivers, pilots, and other individuals operating vehicles or machinery should remain alert, awake, and focused. Keeping vehicle drivers alert and focused is important to their personal safety, the safety of their passengers, and the safety of other drivers and passengers on the road. There is a need for methods and systems that can assist individuals in remaining alert, awake, or focused.

BRIEF SUMMARY

One embodiment is a system for delivery of ultra-low radio frequency energy to an individual to assist the individual to remain, or become, alert, awake, or focused. The system includes at least one delivery coil configured for placement at an effective distance from the individual and a delivery device that includes at least one memory; at least one data file stored, or storable, in the at least one memory, the at least one data file configured for producing signals derived from measurements of at least one molecule, wherein the signals are configured to produce the ultra-low radio frequency energy that assists the individual to remain, or become, alert, awake, or focused when delivered to the at least one delivery coil; and at least one processor coupled to the at least one memory and the at least one delivery coil. The at least one processor is configured to perform actions that include directing generation of the signals using the at least one data file and directing delivery of the signals to the at least one delivery coil to produce the ultra-low radio frequency energy.

Another embodiment is a method for delivery of ultra-low radio frequency energy to an individual to assist the individual to remain, or become, alert, awake, or focused. The method includes generating signals using at least one data file, wherein the at least one data file is configured for producing signals derived from measurements of at least one molecule, wherein the signals are configured to produce the ultra-low radio frequency energy that assists the individual to remain, or become, alert, awake, or focused when delivered to the at least one delivery coil; and directing delivery of the signals to at least one delivery coil placed at an effective distance from the individual to produce the ultra-low radio frequency energy.

In at least some embodiments, at least one of the at least one data file is configured for producing the signals derived, at least in part, from the measurements of a stimulant molecule. In at least some embodiments, the stimulant molecule is selected from nicotine, caffeine, theobromine, or any combination thereof. In at least some embodiments, at least one of the at least one data file is configured for producing the signals derived, at least in part, from the measurements of a combination of two or more molecules.

In at least some embodiments, the at least one delivery coil is disposed in or on a headrest or a seat. In at least some embodiments, the at least one delivery coil is disposed in or on a steering wheel. In at least some embodiments, the at least one delivery coil is disposed in or on a window, or windshield.

In at least some embodiments, the system further includes at least one sensor configured for communication with the delivery device. In at least some embodiments, at least one of the at least one sensor is a physiological or biometric sensor. In at least some embodiments, at least one of the at least one sensor is a driving or flight sensor. In at least some embodiments, the directing generation of the signals includes directing the generation of the signals in response to the at least one sensor. In at least some embodiments, the at least one processor includes instructions for operation of an artificial intelligence configured to receive information from the at least one sensor and determine when to generate the signals in response to the at least one sensor. In at least some embodiments, the artificial intelligence is configured for determining when the individual is drowsy from the information received from the at least one sensor.

In at least some embodiments, the at least one processor includes instructions for manually directing the generation of the signals by the individual. In at least some embodiments, at least one of the at least one data file is a data file using an audio file format.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1:
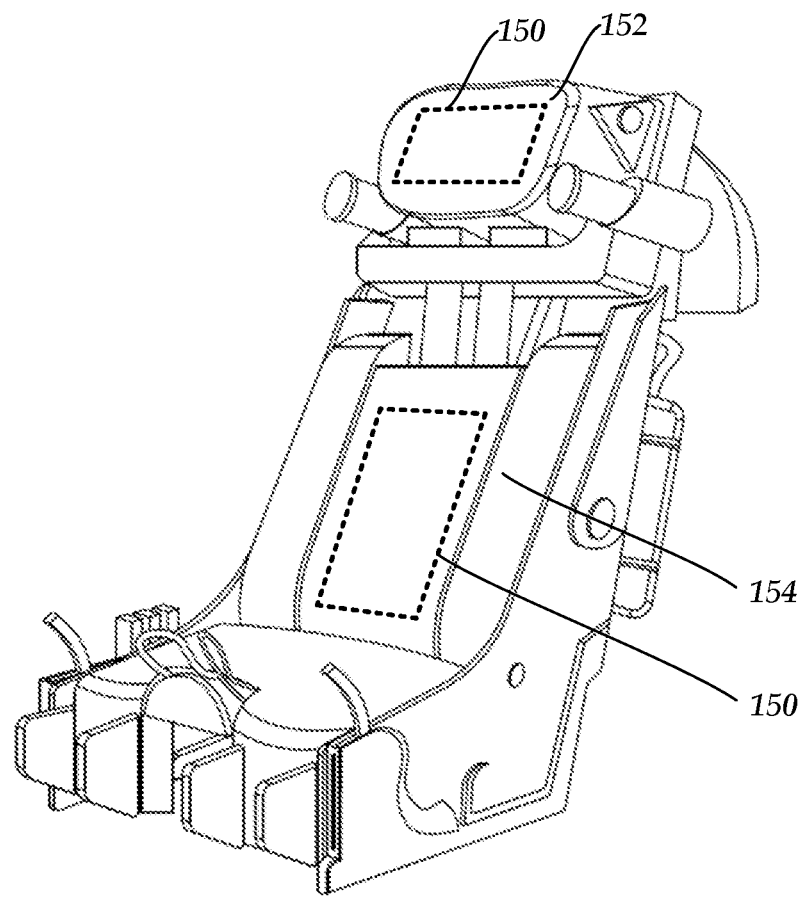
FIG. 1 is a schematic illustration of one embodiment of a seat with a delivery coil disposed on, embedded in, or otherwise attached to a headrest or seat back, according to the invention.

The present invention is directed to the area of systems and methods for assisting individuals in remaining alert, awake, focused, or otherwise stimulated by electromagnetic delivery of signals from a data file. The present invention is also directed to systems and methods for delivery of electromagnetic signals arising from measurements using a stimulant to facilitate assisting individuals in remaining alert, awake, focused, or otherwise stimulated.

Systems and methods to keep a driver, pilot, or others alert, awake, focused, or otherwise stimulated include delivering signals from a data file, such as an audio file (for example, a WAV file) via a delivery coil of a delivery device. The signals can be used to generate ultra-low radio frequency energy that is delivered as an electromagnetic signal to an individual. For example, the ultra-low radio frequency energy can be delivered using a delivery coil (which can be a single coil or any suitable arrangement of multiple coils) that this is positioned near the individual.

The signals for delivery of ultra-low radio frequency energy can be generated from measurements of electromagnetic characteristics of one or more target molecules, such as the unique electrostatic potential of a target molecule. Every molecule has a unique electrostatic surface potential. This potential influences how a molecule interacts with proteins and other biological agents. Electron and charge transfer are central to many biological processes and are a direct result of interacting surface potentials. Artificial electromagnetic fields (e.g., the ultra-low radio frequency energy) are capable of triggering a similar receptor response and conformational change in the absence of a physical drug or molecular agonist.

In at least some embodiments, the unique and specific ultra-low radio frequency energy is used to induce electron and charge transfer in a defined bioactive target, altering cell dynamics to produce a response. In at least some embodiments, to produce a desired response, an ultra-low radio frequency energy cognate of a target molecule is delivered locally and non-systemically via a delivery device. Preclinical and clinical studies suggest that the delivery of ultra-low radio frequency energy provides the ability to specifically regulate metabolic pathways and replicate known mechanisms of action for commercial drugs and other molecules.

Examples of delivery using ultra-low radio frequency energy can be found in U.S. Pat. Nos. 6,724,188; 6,952,652; 6,995,558; 7,081,747; 7,412,340; 9,417,257; 10,046,172; and 11,103,721; U.S. Provisional Patent Application Ser. Nos. 63/164,022 and 63/252,986; U.S. Patent Application Publications Nos. 2019/0143135 and 2019/0184188; and PCT Patent Application Publication WO 2019/070911, all of which are incorporated herein by reference in their entireties. In at least some embodiments, the delivery of ultra-low radio frequency energy includes the generation of a magnetic field having a field strength of up to 1 Gauss. In at least some embodiments, the delivery of ultra-low radio frequency energy includes the generation of a therapeutic magnetic signal having one or more frequencies (or ranges/bands of frequencies) in the range of 0.1 Hz to 22 kHz or in the range of 1 Hz to 22 kHz.

The signals for delivery of ultra-low radio frequency energy can be generated from measurements made using one or more particular target molecules. These measurements can be, for example, processed, converted from analog to digital signals, and stored for delivery using any suitable delivery device, as described in more detail below. The molecule(s) used to obtain the signals can be any suitable drug molecule(s), therapeutic molecule(s), other molecule(s) that produce(s) a physiological or biological response, or the like.

The signals for the data file can be derived from a solvated chemistry (e.g., molecules) and recorded using a SQUID magnetometer, other magnetometry device, a magnetoresistive sensor (described in more detail below), or any other suitable magnetic field sensor. Examples of such files and methods of obtaining such files are presented in, for example, U.S. Pat. Nos. 8,838,022; 8,929,809; 9,300,367; 9,455,771; 9,742,471; and 10,015,623, all of which are incorporated herein by reference in their entireties. The data file may be derived from one or more solvated chemistries.

Examples of molecules that can be particularly useful for assisting a driver, pilot, or other individual to remain alert, awake, focused, or otherwise stimulated can include, but are not limited to, nicotine, caffeine, theobromine, or other stimulant molecules. Signals may be generated for a single molecule, different concentrations of a molecule (for example, different caffeine concentrations), for different combinations/concentrations of two or more molecules (for example, combinations of caffeine and theobromine at different concentrations), or the like.

In at least some embodiments, the signals for delivery of ultra-low radio frequency energy based on one or more particular molecules can be stored as a data file that can be used by the delivery device to provide the ultra-low radio frequency energy. In at least some embodiments, the data file can utilize an audio file format (for example, a WAV, PCM, AIFF, MP3, AAC, WMA, FLAC, ALAC, MIDI, APE, MP2, M4A, AAC, VQF, AMR, AC3, RA, 3GA, OGG, ASF, DSD, or MQA file format, or any other suitable format). Audio file formats may be particularly useful as these formats are used to store multi-frequency information for generating electromagnetic signals. A WAV file is used herein as an example of the data file for storage and delivery of the signals to produce ultra-low radio frequency energy. A suitable resolution can be used including, but not limited to, 16, 24, or 32 bit resolution.

In at least some embodiments, the delivery device can use any suitable method of delivery of the signals from the data file including, but not limited to, analog or digital modulation for signal transmission. Any suitable modulation technique can be used including, but not limited to, any type of amplitude, frequency, phase, or other modulation.

Figure 2:
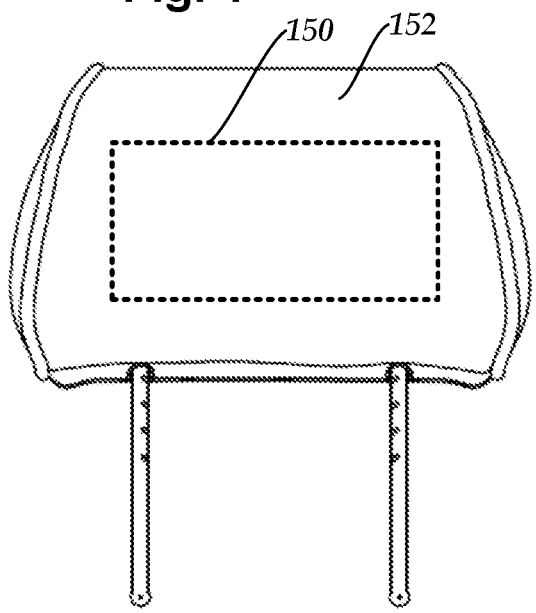
FIG. 2 is a schematic illustration of one embodiment of a headrest with a delivery coil disposed on, embedded in, or otherwise attached to the headrest, according to the invention.
Figure 3:
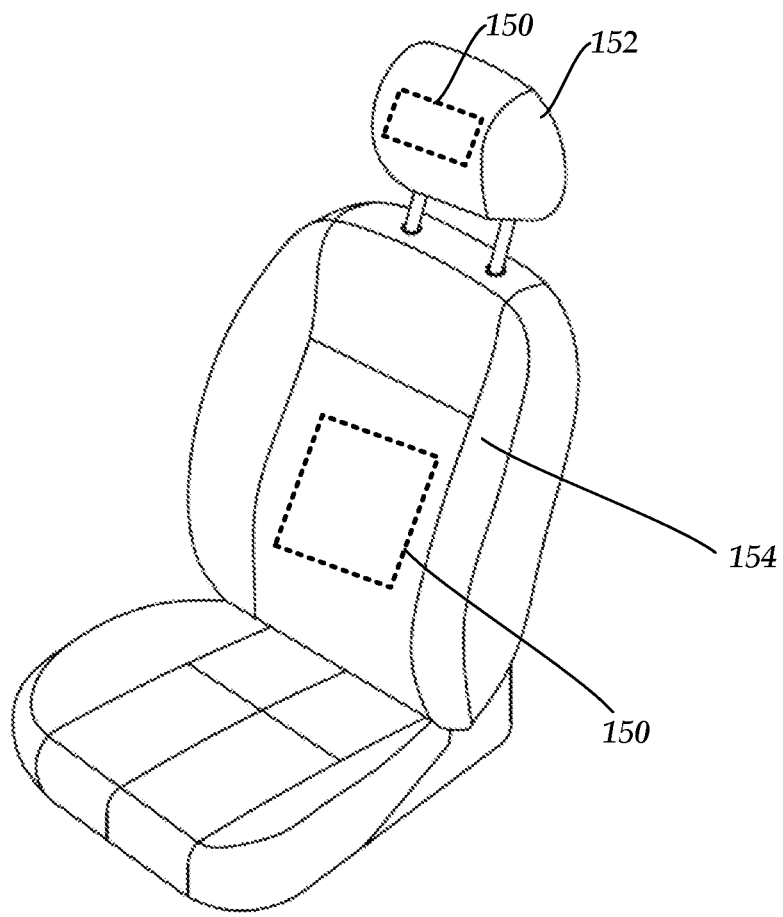
FIG. 3 is a schematic illustration of another embodiment of a seat with a delivery coil disposed on, embedded in, or otherwise attached to a headrest or seat back, according to the invention.
Figure 4:
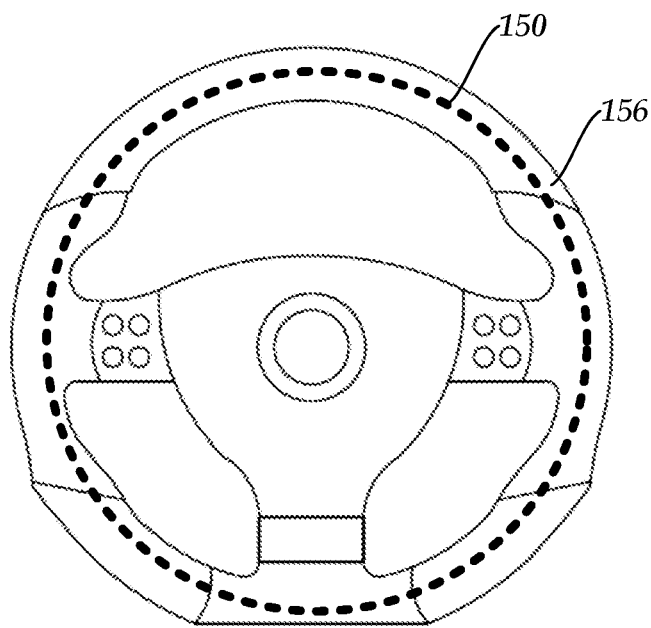
FIG. 4 is a schematic illustration of one embodiment of a steering wheel with a delivery coil disposed on, embedded in, or otherwise attached to the steering wheel, according to the invention.
Figure 5:
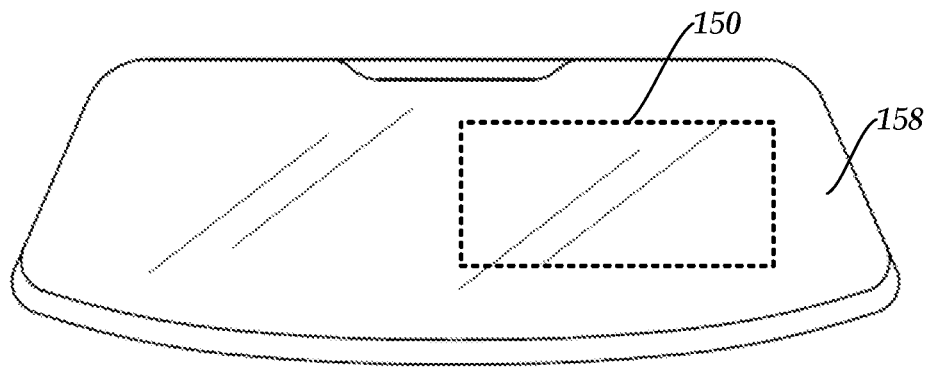
FIG. 5 is a schematic illustration of one embodiment of a windshield of a vehicle with a delivery coil disposed on, embedded in, or otherwise attached to the windshield, according to the invention.
Figure 6:
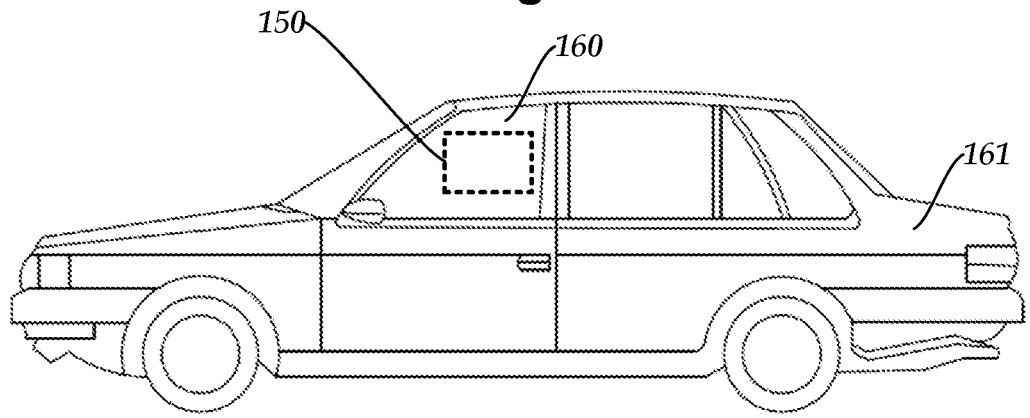
FIG. 6 is a schematic illustration of one embodiment of a vehicle with a delivery coil disposed on, embedded in, or otherwise attached to the window of the vehicle, according to the invention.

Systems and methods to keep a driver, pilot, or others alert, awake, focused, or otherwise stimulated include delivering signals from a data file, such as an audio file (for example, a WAV file,) via a delivery coil 150 (with any suitable coil geometry) of a delivery device. The delivery coil 150 can be a single coil or multiple coils that are, at least in some embodiments, in electrical communication with each other. In at least some embodiments, the delivery coil can be disposed on, embedded in, or otherwise attached to a component such as, for example, a headrest 152 as illustrated in FIGS. 1, 2, and 3; a seat 154 as illustrated in FIGS. 1 and 3; a steering wheel 156, as illustrated in FIG. 4; any other suitable component that can be positioned near or adjacent to an individual (for example, an armrest, seat bottom, portion of the vehicle structure, dashboard, vehicle floor, or the like or any combination thereof); or the like or any combination thereof. This component (e.g., headrest 152, seat 154, steering wheel 156, or the like) can be part of any suitable vehicle including, but not limited to, a car, truck, commercial equipment, military vehicle, military equipment, aircraft, or the like. Additionally or alternatively, the delivery coil 150 can be located above or adjacent the body or head of the driver or pilot. For example, the delivery coil 150 of the delivery device can be disposed in, or on, the ceiling of a car, truck, aircraft, or other vehicle; a glass canopy of an airplane or other vehicle; a windshield 158 (FIG. 5) or a window 160 (FIG. 6) of any vehicle 161, machinery, or aircraft; or the like. The delivery coil 150 is positioned, or capable of being positioned, at a distance from an individual, such as a driver or a pilot, that allows for effective delivery of the ultra-low radio frequency energy. Effective delivery is the delivery of the ultra-low radio frequency energy which produces an effect on the individual to assist the individual to remain (or become) alert, awake, focused, or otherwise stimulated.

Figure 7:
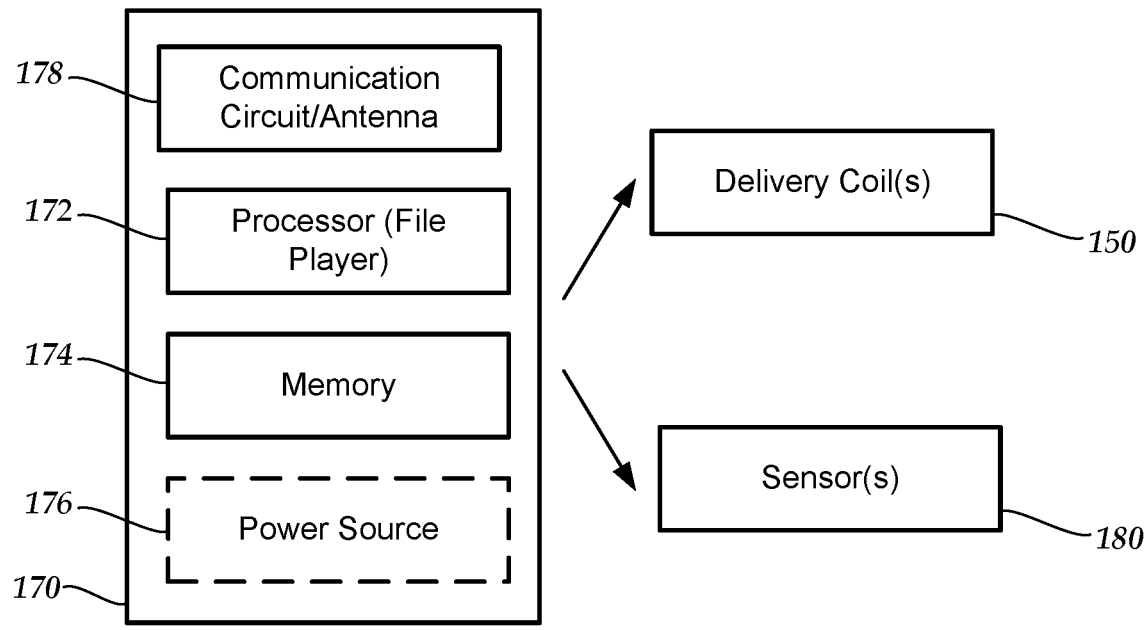
FIG. 7 is a schematic block diagram of one embodiment of a delivery device, according to the invention.

FIG. 7 illustrates one embodiment of a delivery device 170. The delivery device 170 includes a processor 172, a memory 174, an optional power source 176 (for example, a battery), and a communication circuit/antenna 178. The delivery device 170 includes, is attached to, or is in communication with at least one delivery coil 150. In at least some embodiments, the delivery device 170 includes, is attached to, or is in communication with at least one sensor 180 for monitoring an individual. The delivery device 170 can be a separate device or can be incorporated into the vehicle. For example, the delivery device 170 can be incorporated into an entertainment system or a display/console of a vehicle.

Any suitable processor 172 can be used including, but not limited to, microprocessors, application specific integrated circuits (ASICs), other integrated circuits, or the like or any combination thereof. Any suitable memory 174 can be used including, but not limited to, RAM, ROM, EEPROM, flash memory, or the like or any combination thereof.

In at least some embodiments, the delivery device 170 receives power from the vehicle or other arrangement in which the delivery device is disposed. In other embodiments, the delivery device includes a power source 176. The power source 176 can be any suitable power source including, but not limited to, batteries, power cells, or the like or any combination thereof. In at least some embodiments, the power source is rechargeable.

In at least some embodiments, the communication circuit/antenna 178 can include hardwiring to the delivery coil(s) 150 or sensor(s) 170 or any combination thereof. In at least some embodiments, the communication circuit/antenna 178 can be capable of wireless transmission to the delivery coil 150 or sensor(s) 170 or any combination thereof. In at least some embodiments, the delivery device 170 can employ communications arrangements such as NFMI (near field magnetic induction), Bluetooth™, or other wireless communications systems to, for example, transmit the data file from the delivery device to a delivery coil 150 or transmit information from one or more sensors 180 to the delivery device 170.

The sensor(s) 180 produce(s) sensor signals based on observation of an individual, such as a driver, pilot, or the like; on observation of the vehicle or other arrangement in which the delivery coil is disposed; or the like or any combination thereof. These sensor signals may be raw output of the sensor or may be processed (for example, using the processor 172 or other processing circuitry) to produce modified output of the sensor or even data based on the raw output of the sensor. Examples of sensors include, but are not limited to, physiological or biometric sensors (e.g., sensors to monitor heart rate, blood pressure, electroencephalogram, electrocardiogram, blood oxygen level, or the like or any combination thereof), sensors for monitoring the individual (e.g., sensors to monitor eye movement, eye position, gaze, face movement, face position, posture, time to react to an unexpected event, or the like or any combination thereof), sensors to monitor the operation of the vehicle (e.g., sensors to monitor steering or steering patterns, vehicle lane position, vehicle lane deviations, driving corrections, speed, speed variations, aircraft altitude, aircraft attitude, aircraft yaw, or the like or any combination thereof), or the like or any combination thereof.

In at least some embodiments, the processor 172 of the delivery device 170 employs a data file player (for example, a WAV file player) or other data file transmission device (for example, an audio or WAV file transmission device). In at least some embodiments, the delivery device 170 can be used with or without data collection from the sensor(s) 180. In at least some embodiments, the delivery device 170 can operate automatically (or in an automatic mode) using the sensor(s) 180 to monitor the individual.

In at least some embodiments, the processor 172 of the delivery device 170 may incorporate artificial intelligence to operate the delivery device. In at least some embodiments, delivery of the signals by the delivery device 170 can be turned ON or OFF by the sensor(s) or the artificial intelligence or any combination thereof. In at least some embodiments, the artificial intelligence can utilize machine learning to facilitate automated operation of the delivery device 170. In at least some embodiments, the artificial intelligence receives information from the sensors 180 and fuses that information into a decision whether to turn ON or OFF the delivery device 170. Commercial systems that are capable of determining when a driver or pilot is drowsy or otherwise inattentive and sending a warning to the driver are known.

In at least some embodiments, the delivery device 170 makes a ON or OFF decision by collecting driving or flight data (optionally in real time) or the like. As an example, in the case of fighter pilots, the delivery device or delivery system can collect biometric data in addition to flight data to make a ON or OFF decision. In at least some embodiments, biometric data from physiological or biometric sensors can be used in combination with driving or flight information.

In at least some embodiments, the delivery device 170 can be manually controlled and may be arranged to be solely manually controlled or solely manually controlled when such operation is selected by a user. In at least some embodiments, the delivery device 170 can be manually turned ON or OFF. In at least some embodiments, a driver or pilot can manually turn ON the delivery device 170, for example, when the driver or pilot becomes drowsy behind the wheel, and the driver or pilot can later manually turn OFF the delivery device.

In at least some embodiments, manual or automated control of the delivery device 170 can also include selection of the signals to be delivered to the delivery coil 150. For example, selection of the signals can include selection of a signal (or a combination of signals) corresponding to a molecule or a combination of molecules, selection of a signal corresponding to a concentration of one or more of the molecules, selection of an amplitude (or intensity) of the signals, or the like or any combination thereof.

In at least some embodiments, the delivery coil 150 delivers the signals in a range of 20 to 40 mG (2 to 4 µT). In at least some embodiments, the signals are delivered periodically with a periodicity determined by the user or the system (e.g., by an artificial intelligence or by system programming) or programmed into the system.

Figure 8:
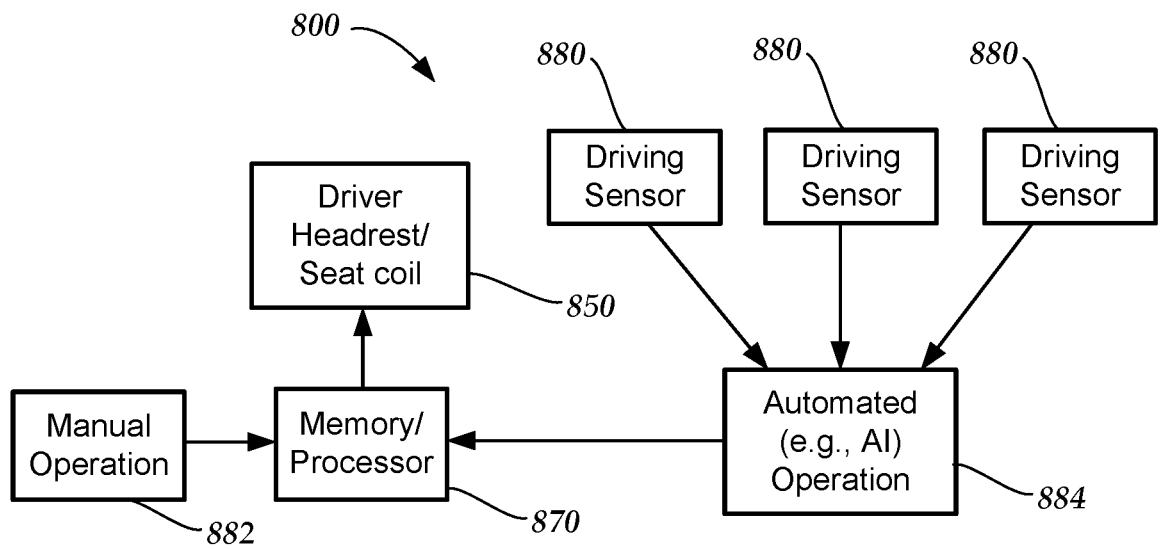
FIG. 8 is a schematic block diagram of one embodiment of a delivery system for an automobile or truck, according to the invention.

FIG. 8 illustrates one embodiments of a system 800 for an automobile or truck or the like. The system 800 includes a coil 850 in the driver headrest or seat (or elsewhere in the vehicle) or any combination of these sites. The system also includes the memory/processor 870 or a delivery device (see, FIG. 7) in communication with the coil 850. In at least some embodiments, the delivery device allows for manual operation 882 or automated operation 884 utilizing one or more driving sensors 880.

Figure 9:
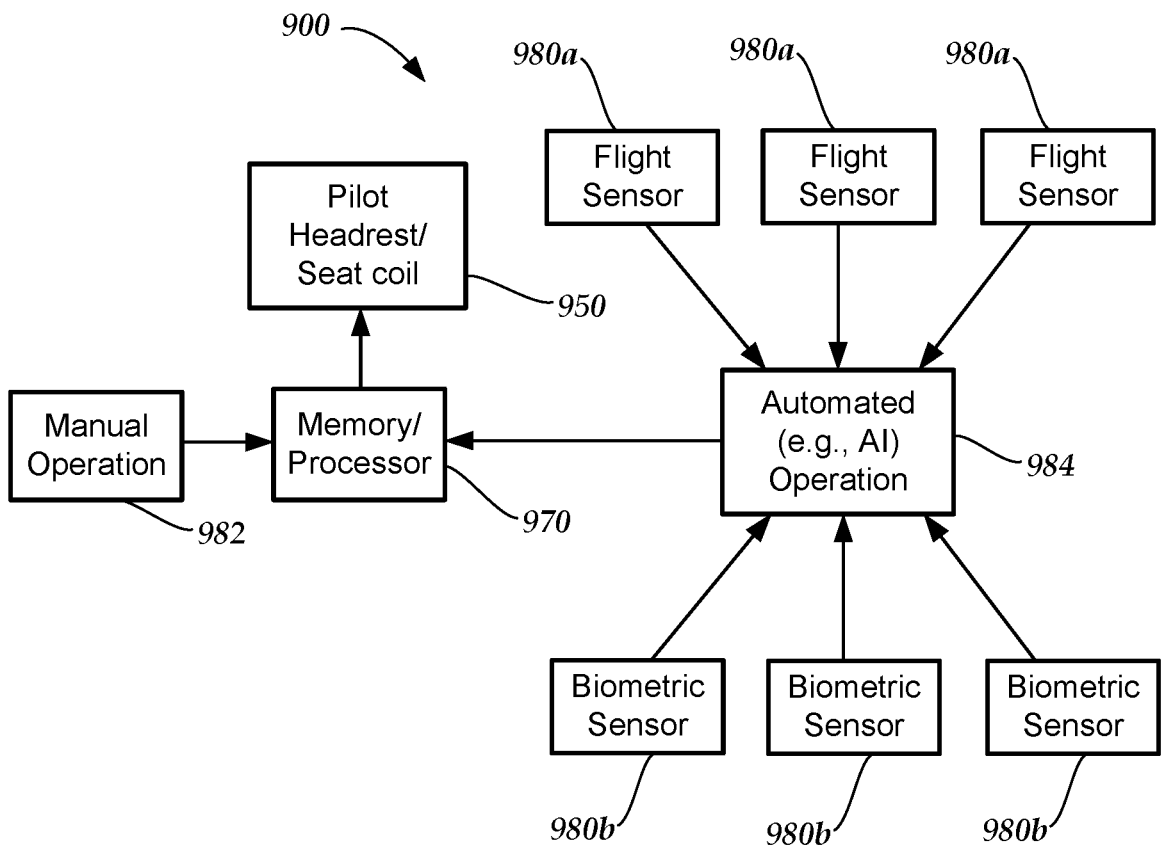
FIG. 9 is a schematic block diagram of one embodiment of a delivery system for an airplane, according to the invention.

FIG. 9 illustrates one embodiments of a system 900 for an airplane or the like. The system 900 includes a coil 950 in the pilot headrest or seat (or elsewhere in the airplane) or any combination of these sites. The system also includes the memory/processor 970 or a delivery device (see, FIG. 7) in communication with the coil 950. In at least some embodiments, the delivery device allows for manual operation 982 or automated operation 984 utilizing one or more flight sensors 980$a$ and biometric sensors 980$b$.

The signals for delivery of ultra-low radio frequency energy can be generated from measurements made using one or more particular target molecules. These measurements can be obtained using any suitable sensor including, but not limited to, superconducting quantum interference device (SQUID) sensors, magnetoresistive (MR) sensors, optically pumped magnetometer (OPM) sensors, other magnetometer sensors (for example, nitrogen vacancy magnetometers), or the like or any combination thereof.

In at least some embodiments, the measurements of a solvated molecule can be dynamic or non-linear and may be obtained over a period of time ranging from seconds to minutes or longer. In at least some embodiments, the measurements are made at or near room temperature. In at least some embodiments, the measurements can be made at a sampling rate of 40 kHz or higher.

As an example, a magnetoresistive (MR) sensor can be used in a single or multi-channel configuration to measure the magnetic field of a solvated target molecule and produce measurement signals. The measurement signals are processed and stored (for example, as a 24-bit WAV file). In at least some embodiments, the bandwidth of the stored measurement signals is in a range from DC to 22 kHz or more. In at least some instances, particularly when using an MR sensor, the bandwidth is in a range of 0.1 Hz to 10 kHz.

Figure 10:
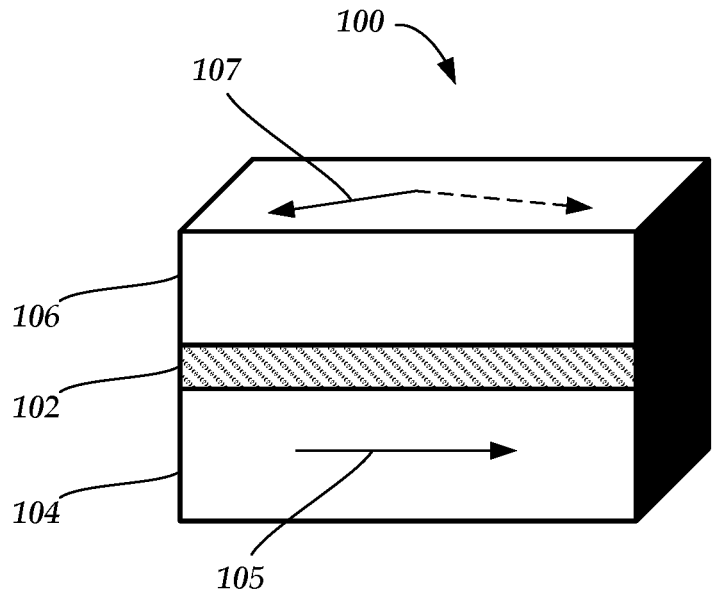
FIG. 10 is a diagram of one embodiment of a magnetoresistive (MR) sensor.

FIG. 10 illustrates one embodiment of a magnetoresistive (MR) sensor 100 (which is also known as a tunnel magnetoresistive (TMR) sensor or magnetic tunnel junction (MTJ) sensor) that includes a thin film 102 of non-magnetic material between two ferromagnetic films that form a pin layer 104 and a free layer 106, respectively. The pin layer 104 has a direction of magnetization 105 that is pinned. Pinning can be accomplished by a variety of methods including forming the pin layer 104 of a material in a defined crystal structure. The direction of magnetization 107 of the free layer 106 follows the direction of an external magnetic field. For example, the free layer 106 can be formed of a material in an amorphous (e.g., non-crystalline) structure. Examples of MR devices are found in, for example, European Patent Application No. EP 2614770, incorporated herein by reference in its entirety.

The electrical resistance of the magnetoresistive sensor 100 varies (in at least some embodiments, proportionally) with a relative angle between the directions of magnetization in the pin layer 104 and the free layer 106. Thus, by observing the resistance of the magnetoresistive sensor 100, the direction of the external magnetic field can be determined.

Figure 11:
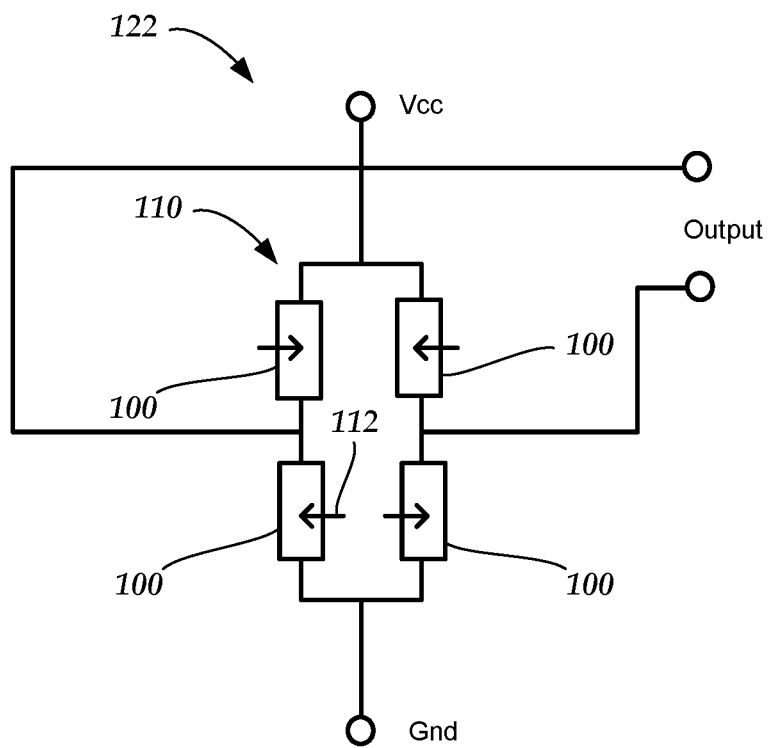
FIG. 11 illustrates one embodiment of an arrangement of MR sensors in a Wheatstone bridge for temperature compensation.

One or more MR sensors 100 can be used to measure the magnetic field by coupling to a DC power source. In FIG. 11, a MR sensor device 122 includes a Wheatstone bridge arrangement 110 of four MR sensors 100 (where the arrows 112 indicate the direction of magnetization of the pin layer 106) can be used for differential temperature compensation. One example of a MR sensor device that utilizes the MR sensors 100 is the TDK Nivio xMR Sensor (TDK Corporation, Tokyo, Japan).

Figure 12:
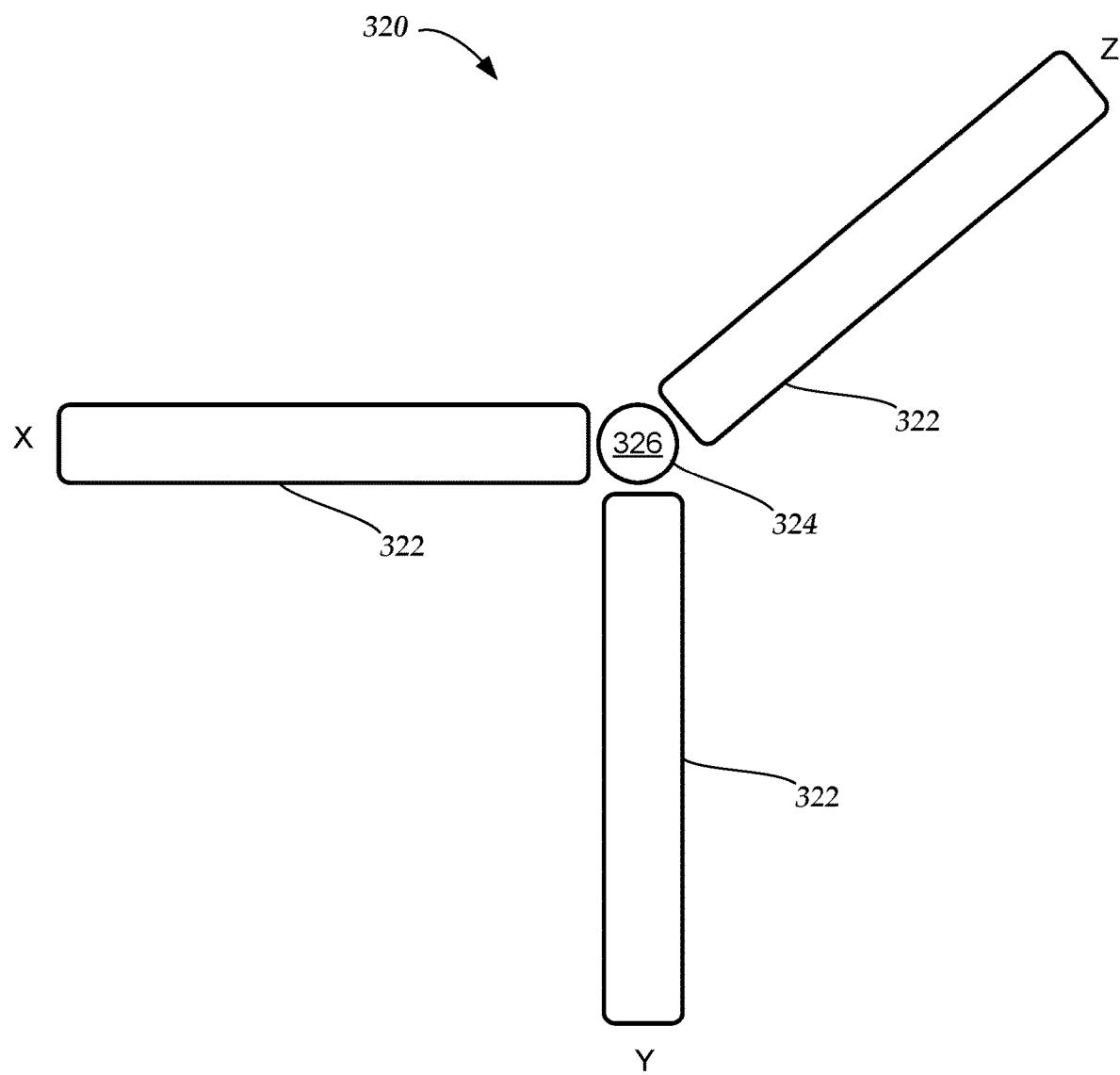
FIG. 12 is a schematic diagram of one embodiment of an arrangement of MR sensor devices around a container of solvated target molecule, according to the invention.

FIG. 12 illustrates one embodiment of a sensor arrangement 320 with multiple MR sensor devices 322 disposed around a container 324 with the target molecule 326 solvated in a solvent (for example, water, saline, phosphate buffered saline (PBS), plasma, or blood). The target molecule 326 can be any suitable target including, but not limited to, drug molecules (e.g., Taxol), oligonucleotides (e.g., RNA, mRNA, or the like), or any combination thereof.

In the illustrated embodiment, a MR sensor device 322 is positioned at the x, y, and z axes to measure the magnetic field arising from the electrostatic potential of the target molecule. Such measurement may include, for example, injecting noise into the sample in the container and recording the resulting magnetic field, as described in the references cited above. In at least some embodiments, the MR sensor device 322 can be a single MR sensor 100 or can be multiple MR sensors 100 arranged in the bridge illustrated in FIG. 11 or any other suitable arrangement.

Figure 13:
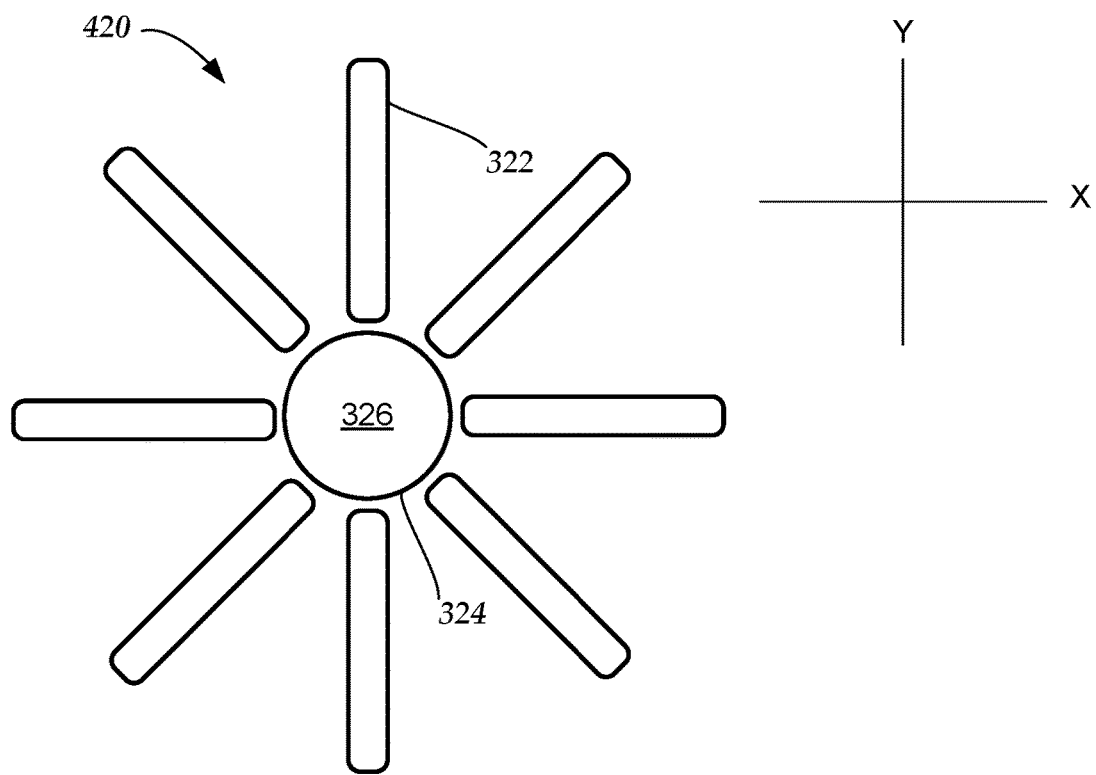
FIG. 13 is a schematic diagram of another embodiment of an arrangement of MR sensor devices around a container of solvated target molecule, according to the invention.

FIG. 13 illustrates another embodiment of a sensor arrangement 420 with multiple MR sensor devices 322 disposed around the container 324 with the solvated target molecule. In this particular arrangement, eight MR sensor devices 322 are arranged around the container in the x-y plane.

Figure 14:
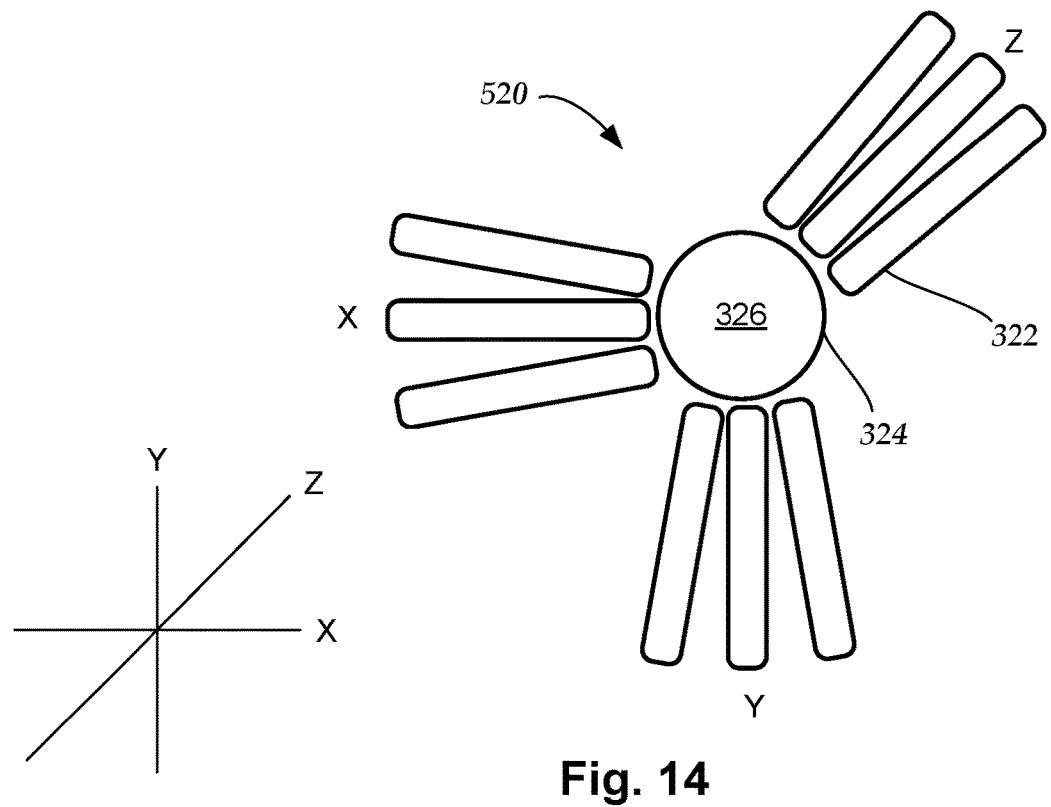
FIG. 14 is a schematic diagram of a third embodiment of an arrangement of MR sensor devices around a container of solvated target molecule, according to the invention.

FIG. 14 illustrates a further embodiment of a sensor arrangement 520 with multiple MR sensor devices 322 disposed around the container 324 with the solvated target molecule. In this particular arrangement, three MR sensor devices 322 are arranged around each of the x, y, and z axes. It will be recognized that other three-dimensional arrangements of MR sensor devices can be used including, for example, providing the arrangement illustrated in FIG. 13 along multiple planes (for example, the x-y plane and the y-z plane).

The arrangements of MR sensor devices 322 illustrated in FIGS. 12, 13, and 14 are examples of multi-channel configurations for recording the electrostatic potential of a target molecule. It will be understood that single channel configurations with a single MR sensor device (or multiple MR sensor devices positioned together) can also be used.

Figure 15:
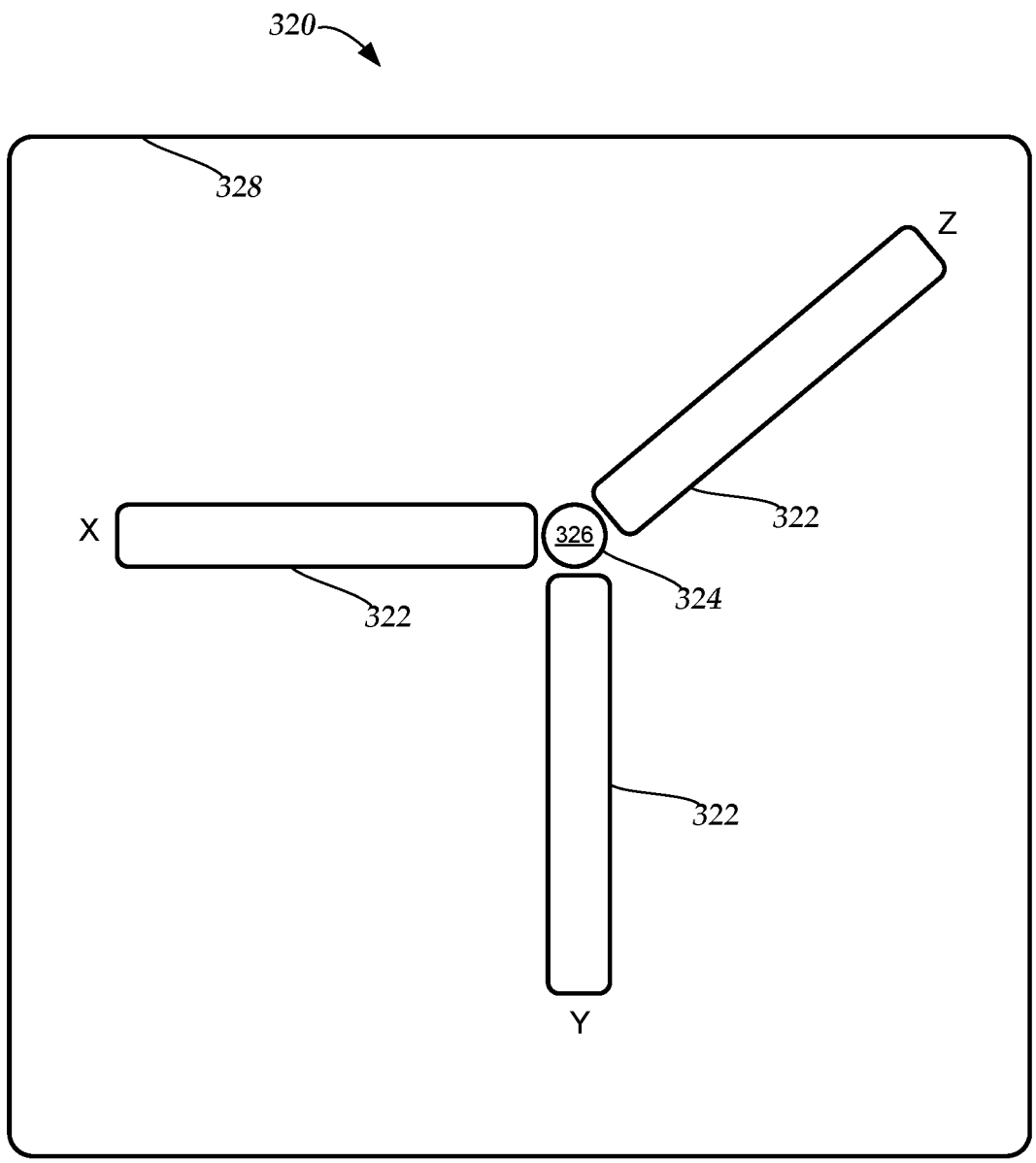
FIG. 15 is a schematic diagram of the arrangement of MR sensor devices around a container of solvated target molecule of FIG. 3 inside a shield, according to the invention.

FIG. 15 illustrates the sensor arrangement of 320 disposed within a shield 328 to reduce or remove the ambient magnetic field (such as the Earth's magnetic field) within the shield. The shield can be a passive shield (for example, made of mu-metal or other shielding material or a Faraday cage or the like) or an active shield (for example, one or more magnetic field generators to counter the ambient magnetic field) or any combination thereof.

Figure 16:
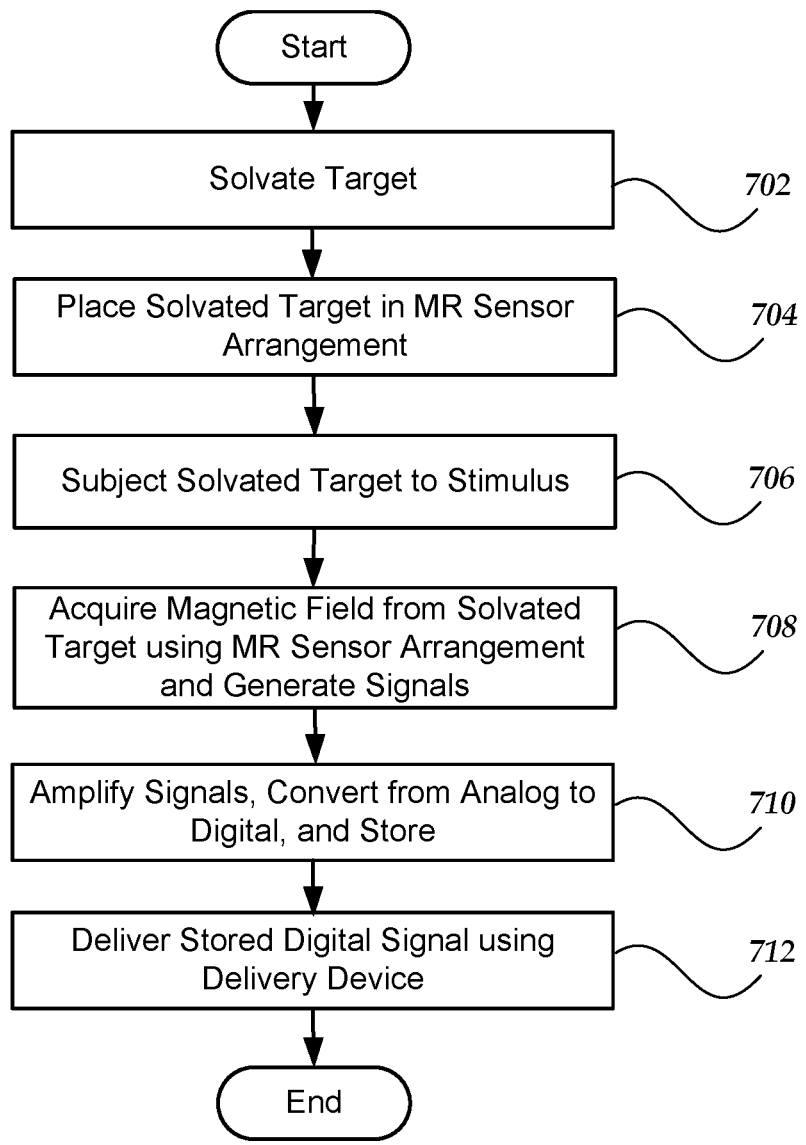
FIG. 16 is one embodiment of a method for generating and employing ultra-low radio frequency energy using MR sensor devices, according to the invention.

FIG. 16 illustrates one embodiment of a workflow for generating and employing ultra-low radio frequency energy using the MR sensor devices described herein. In step 702, the target molecule is solvated in a solvent, such as, for example, water, saline, PBS, plasma, or blood. In step 704, the solvated target is placed in a MR Sensor arrangement, such as one of those illustrated in FIG. 12, 13, or 14, or any other multi-channel or single channel configuration or arrangement.

In step 706, the solvated target is subjected to a stimulus (for example, noise or other suitable signal) to elicit a response. In step 708, the MR sensor devices of the MR sensor arrangement acquire the magnetic field generated by the solvated target and the MR sensor devices generate signals based on the acquired magnetic field. In step 710, the signals from the MR sensor devices are amplified or otherwise processed, converted from analog to digital signals, and stored.

In step 712, the stored digital signals are then provided to a delivery device, such as the delivery device 170, to deliver the signals to a target and elicit the desired response based on the initial target molecule.

The above specification provides a description of the invention and the manufacture and use of the invention. Since many embodiments of the invention can be made without departing from the spirit and scope of the invention, the invention also resides in the claims hereinafter appended.

What is claimed as new and desired to be protected is:

1. A system for delivery of ultra-low radio frequency energy to an individual the system comprising:
    at least one delivery coil configured for placement at an effective distance from the individual; and
    a delivery device comprising
        at least one memory;
        at least one data file stored, or storable, in the at least one memory, the at least one data file configured for producing signals derived from measurements of at least one molecule, wherein the signals are configured to produce the ultra-low radio frequency energy when delivered to the at least one delivery coil, wherein at least one of the at least one data file is configured for producing the signals derived, at least in part, from the measurements of at least one molecule selected from nicotine, caffeine, theobromine, or any combination thereof; and
        at least one processor coupled to the at least one memory and the at least one delivery coil, wherein the at least one processor is configured to perform actions, comprising
            directing generation of the signals using the at least one data file, and
            directing delivery of the signals to the at least one delivery coil to produce the ultra-low radio frequency energy.

2. The system of claim 1, wherein the at least one delivery coil is disposed in or on a headrest or a seat.

3. The system of claim 1, wherein the at least one delivery coil is disposed in or on a steering wheel.

4. The system of claim 1, wherein the at least one delivery coil is disposed in or on a window, or windshield.

5. The system of claim 1, further comprising at least one sensor configured for communication with the delivery device.

6. The system of claim 5, wherein at least one of the at least one sensor is a physiological or biometric sensor.

7. The system of claim 5, wherein at least one of the at least one sensor is a driving or flight sensor.

8. The system of claim 5, wherein the directing generation of the signals comprises directing the generation of the signals in response to the at least one sensor.

9. The system of claim 1, wherein the at least one processor comprises instructions for manually directing the generation of the signals by the individual.

10. The system of claim 1, wherein at least one of the at least one data file is a data file using an audio file format.

11. A system for delivery of ultra-low radio frequency energy to an individual the system comprising:
    at least one delivery coil configured for placement at an effective distance from the individual; and
    a delivery device comprising
        at least one memory;
        at least one data file stored, or storable, in the at least one memory, the at least one data file configured for producing signals derived from measurements of at least one molecule, wherein the signals are configured to produce the ultra-low radio frequency energy when delivered to the at least one delivery coil, wherein at least one of the at least one data file is configured for producing the signals derived, at least in part, from the measurements of a combination of two or more molecules; and
        at least one processor coupled to the at least one memory and the at least one delivery coil, wherein the at least one processor is configured to perform actions, comprising
            directing generation of the signals using the at least one data file, and
            directing delivery of the signals to the at least one delivery coil to produce the ultra-low radio frequency energy.

12. The system of claim 11, wherein at least one of the two or more molecules is selected from nicotine, caffeine, or theobromine.

13. A system for delivery of ultra-low radio frequency energy to an individual the system comprising:

at least one delivery coil configured for placement at an effective distance from the individual;

at least one sensor configured for communication with the delivery device; and a delivery device comprising at least one memory;

at least one data file stored, or storable, in the at least one memory, the at least one data file configured for producing signals derived from measurements of at least one molecule, wherein the signals are configured to produce the ultra-low radio frequency energy when delivered to the at least one delivery coil; and at least one processor coupled to the at least one memory and the at least one delivery coil, wherein the at least one processor is configured to perform actions, comprising directing generation of the signals using the at least one data file, and directing delivery of the signals to the at least one delivery coil to produce the ultra-low radio frequency energy, wherein the at least one processor comprises instructions for operation of an artificial intelligence configured to receive information from the at least one sensor and determine when to generate the signals in response to the at least one sensor.

14. The system of claim 13, wherein at least one of the at least one data file is configured for producing the signals derived, at least in part, from the measurements of a stimulant molecule.

15. The system of claim 13, wherein at least one of the at least one data file is configured for producing the signals derived, at least in part, from the measurements of at least one molecule selected from nicotine, caffeine, theobromine, or any combination thereof.

16. The system of claim 13, wherein the artificial intelligence is configured for determining when the individual is drowsy from the information received from the at least one sensor.

17. A method for delivery of ultra-low radio frequency energy to an individual the method comprising:

generating signals using at least one data file, wherein the at least one data file is configured for producing signals derived from measurements of at least one molecule, wherein the signals are configured to produce the ultra-low radio frequency energy when delivered to at least one delivery coil, wherein at least one of the at least one data file is configured for producing the signals derived, at least in part, from the measurements of at least one molecule selected from nicotine, caffeine, theobromine, or any combination thereof; and directing delivery of the signals to at least one delivery coil placed at an effective distance from the individual to produce the ultra-low radio frequency energy.

18. The method of claim 17, wherein the at least one delivery coil is disposed in or on a headrest, a seat, a steering wheel, a window, or windshield.

19. The method of claim 17, wherein the generating the signals comprises generating of the signals in response to the at least one sensor.

20. The method of claim 17, wherein the generating the signals comprises manually directing the generation of the signals by the individual.

* * * * *